United States Patent
Tagge

(10) Patent No.: US 8,070,032 B2
(45) Date of Patent: Dec. 6, 2011

(54) APPARATUS, SYSTEM, AND METHOD FOR MIDDLE TURBINATE MEDIALIZER

(76) Inventor: Bryan C. Tagge, North Salt Lake, UT (US)

( * ) Notice: Subject to any disclaimer, the term of this patent is extended or adjusted under 35 U.S.C. 154(b) by 143 days.

(21) Appl. No.: 12/332,222

(22) Filed: Dec. 10, 2008

(65) Prior Publication Data
US 2009/0149882 A1 Jun. 11, 2009

Related U.S. Application Data

(62) Division of application No. 10/961,280, filed on Oct. 8, 2004, now abandoned.

(60) Provisional application No. 60/509,509, filed on Oct. 8, 2003.

(51) Int. Cl.
*A61B 17/068* (2006.01)

(52) U.S. Cl. ........ 227/175.1; 227/19; 606/222; 128/898

(58) Field of Classification Search .................. None
See application file for complete search history.

(56) References Cited

U.S. PATENT DOCUMENTS

| | | | | |
|---|---|---|---|---|
| 2,327,353 A | * | 8/1943 | Karle | 606/146 |
| 2,577,240 A | * | 12/1951 | Findley | 606/145 |
| 2,751,908 A | * | 6/1956 | Wallace | 606/114 |
| 3,278,107 A | | 10/1966 | Rygg | |
| 3,575,038 A | | 4/1971 | Mallett | |
| 4,484,580 A | * | 11/1984 | Nomoto et al. | 606/146 |
| 4,664,305 A | | 5/1987 | Blake, III et al. | |
| 4,809,695 A | * | 3/1989 | Gwathmey et al. | 227/175.1 |
| 4,841,888 A | * | 6/1989 | Mills et al. | 112/169 |
| 5,020,514 A | * | 6/1991 | Heckele | 600/107 |
| 5,037,021 A | * | 8/1991 | Mills et al. | 227/175.1 |
| 5,040,715 A | | 8/1991 | Green et al. | |
| 5,351,871 A | | 10/1994 | Bauer | |
| 5,361,782 A | | 11/1994 | Bauer | |
| 5,366,134 A | | 11/1994 | Green et al. | |
| 5,370,294 A | | 12/1994 | Bauer | |
| 5,423,858 A | | 6/1995 | Bolanos et al. | |
| 5,474,571 A | * | 12/1995 | Lang | 606/205 |
| 5,484,451 A | * | 1/1996 | Akopov et al. | 606/139 |
| 5,496,338 A | * | 3/1996 | Miyagi et al. | 606/162 |
| 5,520,700 A | * | 5/1996 | Beyar et al. | 606/139 |
| 5,540,240 A | | 7/1996 | Bauer | |

(Continued)

FOREIGN PATENT DOCUMENTS
WO 2007/134215 11/2007

OTHER PUBLICATIONS

Powered LDS Single Use Surgical Stapler, Instruction Manual, United States Surgical, a Division of Tyco Healthcare Group LP, Norwalk, CT 06856, 1995, 2001, 2002.

(Continued)

*Primary Examiner* — Lindsay Low
(74) *Attorney, Agent, or Firm* — Maschoff Gilmore & Israelsen

(57) ABSTRACT

An apparatus, system, and method are disclosed for medializing the middle turbinate following sinus surgery, thus preventing synacheiae, granulation tissue, and other complications of the prior art. The apparatus utilizes a fastening device configured to attach the middle turbinate to the nasal septum, a prong comprising a slender wand portion and a fastening module, and a handle configured to trigger deployment of the fastening means by activating the fastening module. The fastening device may be a staple, rivet, glue, or another similar device.

20 Claims, 16 Drawing Sheets

U.S. PATENT DOCUMENTS

| | | | |
|---|---|---|---|
| 5,571,117 A * | 11/1996 | Ahn | 606/139 |
| 5,573,529 A * | 11/1996 | Haak et al. | 606/1 |
| 5,814,054 A * | 9/1998 | Kortenbach et al. | 606/139 |
| 5,915,615 A | 6/1999 | Bauer | |
| 6,131,790 A | 10/2000 | Piraka | |
| 6,355,032 B1 | 3/2002 | Hovda et al. | |
| 6,565,560 B1 | 5/2003 | Goble et al. | |
| 6,585,744 B1 * | 7/2003 | Griffith | 606/144 |
| 6,743,240 B2 | 6/2004 | Smith et al. | |
| 6,843,794 B2 | 1/2005 | Sixto, Jr. et al. | |
| 7,520,876 B2 * | 4/2009 | Ressemann et al. | 604/510 |
| 2002/0099366 A1 | 7/2002 | Dahla et al. | |
| 2005/0113850 A1 | 5/2005 | Tagge | |
| 2005/0222610 A1 | 10/2005 | Melker | |
| 2006/0163313 A1 | 7/2006 | Larson | |
| 2007/0293946 A1 | 12/2007 | Gonzales et al. | |

OTHER PUBLICATIONS

Roticulator 55 Poly Disposable Surgical Stapler, Instruction booklet, United States Surgical Corporation, Norwalk, Conneticut 06856, 1995.

ENTact Septal Stapler, Entrigue Surgical, http://www.entriguesurgical.com/home/products/entact/need Oct. 22, 2008.

MTM Middle Turbinate Medializer, Entrigue Surgical, http://entriguesurgical.com/home/products/mtm/the_product Oct. 22, 2008.

* cited by examiner

APPARATUS, SYSTEM, AND METHOD FOR MIDDLE TURBINATE MEDIALIZER

CROSS-REFERENCES TO RELATED APPLICATIONS

This application is a divisional application under 37 CFR 1.53(b) of and claiming priority to U.S. patent application Ser. No. 10/961,280 entitled "APPARATUS, SYSTEM, AND METHOD FOR MIDDLE TURBANITE MEDIALIZER" and filed on Oct. 8, 2004 for Bryan C. Tagge, and to U.S. Provisional Patent Application No. 60/509,509 entitled "MIDDLE TURBANITE MEDIALIZER" and filed on Oct. 8, 2003 for Bryan C. Tagge which is incorporated herein by reference. The specification and drawings include no new matter.

BACKGROUND OF THE INVENTION

1. Field of the Invention

This invention relates to devices for surgery and more particularly relates to devices for sinus and nasal surgery.

2. Description of the Related Art

Adherence of the middle turbinates to the lateral wall of the nasal cavity is a common post-operative problem following sinus surgery performed on either the maxillary ethmoid sphenoid or frontal sinuses. This condition, known as synechiae, blocks the middle meatus, or opening to the sinuses, causing persistent sinusitis and sinus disease.

Development of synechiae can require lysing to separate the middle turbinate from the lateral nasal wall. This can be performed under local anesthesia in a doctor's office or under general antisthetic, using endoscopic visualization. It is, however, an additional surgical procedure, inconvenient and often painful for the patient.

Attempts to avoid this problem include placement of a middle meatus spacer consisting of dissolvable or non-dissolvable packing positioned to medialize the turbinate away from the lateral wall. Packing, however, can foster the growth of granulation tissue as the body's inflammatory response to a foreign body. Granulation tissue can cause persistent sinus disease. Another medializing technique employs sutures to secure the middle turbinates to the septum. Placement of the sutures, however, is a time consuming and painstaking process.

Existing surgical instruments such as bowel staplers are not adapted to the environment of the nasal cavity. The existing septum stapling instruments are narrow enough to enter the nasal cavity but are not configured with attachment means of sufficient length and otherwise appropriate to secure the middle turbinate.

From the foregoing discussion, it should be apparent that a need exists for an apparatus, system, and method for reliably medializing the middle turbinate away from the middle meatus with its opening to the sinus. Beneficially, such an apparatus, system, and method would be time effective for the physician as well as safe and comfortable for the patient.

SUMMARY OF THE INVENTION

The present invention has been developed in response to the present state of the art, and in particular, in response to the problems and needs in the art that have not yet been fully solved by currently available surgical instruments. Accordingly, the present invention has been developed to provide an apparatus, system, and method for medializing the middle turbinate that overcome many or all of the above-discussed shortcomings in the art.

The apparatus to medialize the middle turbinate is provided with a fastening module attached to a slender prong configured to enter the nasal cavity. The prong is attached to a handle configured for manipulation of the prong and also configured to activate the fastening module. The prongs are configured to be slender enough to enter the nasal cavity, with the space between them sufficiently wide to accommodate the septum and middle turbinates.

The apparatus, in one embodiment, is configured to enter the nasal cavity between the middle turbinate and lateral wall of the cavity and staple the middle turbinate to the septum.

The apparatus is further configured, in one embodiment, to enter the nasal cavity between the septum and middle turbinate and staple septal membranes, or mucoperichondrial flaps following septoplasty or removal of deformed septal bone and cartilage.

In a further embodiment, the apparatus may be configured to rivet the middle turbinate to the septum. In another embodiment the apparatus may be configured to deploy staples or rivets composed of absorbable or non-absorbable material. In an additional embodiment the apparatus may be configured to suture the middle turbinate to the septum. In yet another embodiment the apparatus may be configured to attach the middle turbinate to the septum via adhesive. In one additional embodiment the apparatus may be configured to attach the middle turbinate to the septum via cauterization.

A system of the present invention is also presented to medialize the middle turbinate. The system may be embodied in the combination of the fastening module, fastening means, prongs and activation handle of the apparatus. In particular, the system, in one embodiment, includes a fastening module configured to staple the middle turbinate to the septum. In a further embodiment the system may include staples comprised of a bioabsorbable material.

The system may further include the fastening module configured to rivet the middle turbinate to the septum. In a further embodiment the system may include rivets comprised of a bioabsorbable material. The system may also include the fastening module configured to suture the middle turbinate to the septum.

The system may further include the fastening module configured to attach the middle turbinate to the septum via adhesive. In a further embodiment the system may include the prong configured with an inner extension configured to apply the adhesive and an outer extension configured to press the middle turbinate against the septum during setting of the adhesive.

The system may further include the fastening module configured to attach the middle turbinate to the septum via cauterization. In a further embodiment the system may include the prong configured with a heatable inner extension configured perform the cauterization and an outer extension configured to press the middle turbinate against the septum following cauterization. In a further embodiment the system may include a removable clamp configured to hold the middle turbinate in place during adhesion of the cauterization.

The system may further include equipment for direct or remote endoscopic visualization of the placement of the fastening means.

A method of the present invention is also presented for medializing the middle turbinate. The method in the disclosed embodiments substantially includes the steps necessary to carry out the functions presented above with respect to the operation of the described apparatus and system. In one embodiment, the method includes preparing the patient, providing the apparatus, inserting the prongs and fastening module of the apparatus in the nasal cavity, activating the fastening module, placing the fastening means, and removing the apparatus. The method also may include placing a removable clamp to hold the turbinate against the septum following cauterization.

In a further embodiment, the method includes direct or remote endoscopic visualization of the procedure.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which: In order that the manner in which the advantages of the invention will be readily understood, a more particular description of the invention will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

Figure 1:
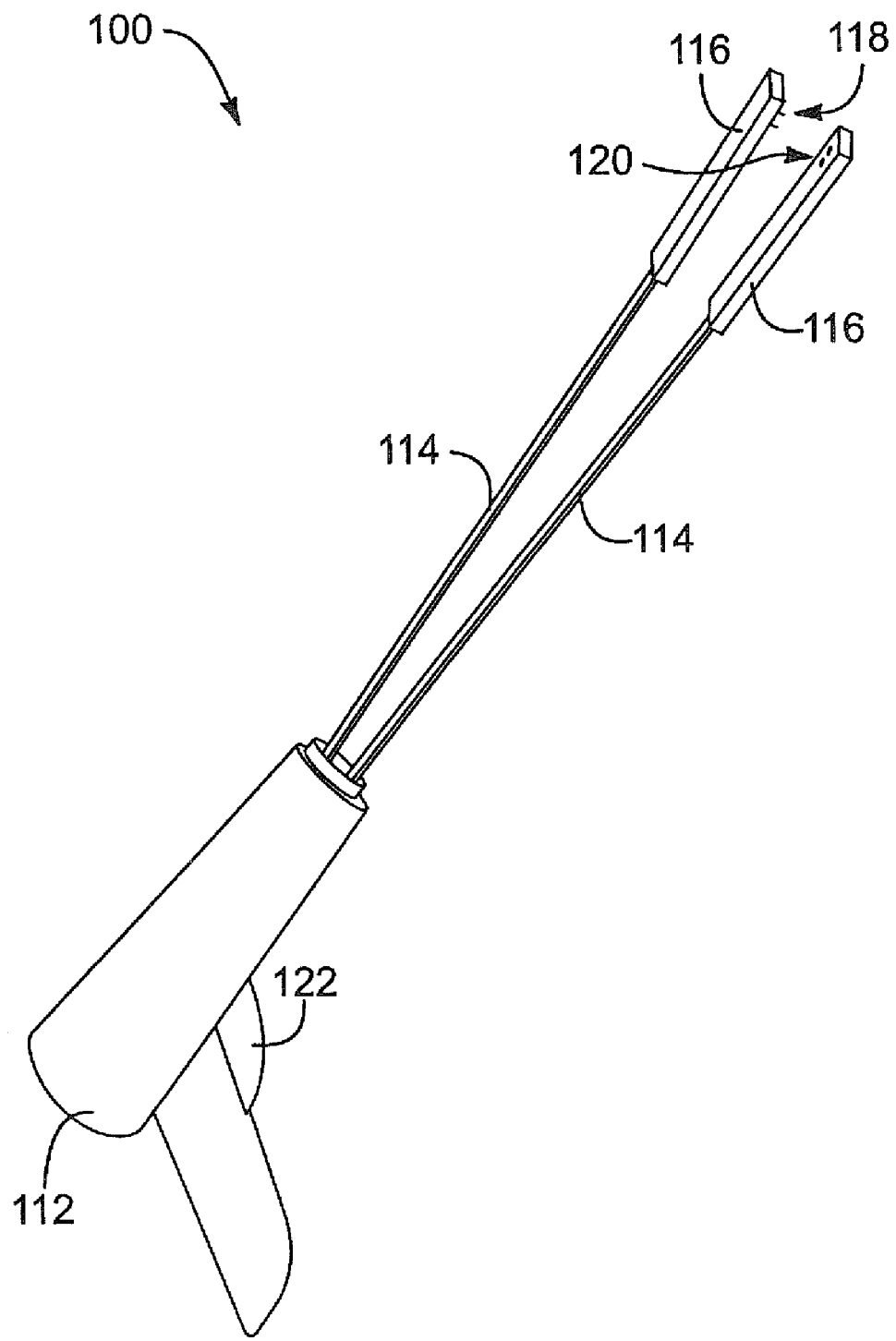
FIG. 1 is perspective view of one embodiment of a middle turbinate medializer in accordance with the present invention.

The invention is a medical instrument, specifically, a middle turbinate medializer. In effect, the medializer is a modification of surgical devices used to attach body tissues following surgery and during healing. The device of the present invention, however, is adapted to being placed up the nose. FIG. 1 illustrates one embodiment of a middle turbinate medializer 100 of the present invention. The medializer 100 is forked, as shown, and comprises a handle 112, two prongs 114, and a fastening module 116 on each prong 114. The fastening module 116 in one embodiment receives a fastener such as a staple 118 and a base 120. The staple 118 is held by one prong 114 and the base held on the other prong 114. The staple 118 is preferably configured to be sufficiently long to pass through one middle turbinate, the septum, and the opposite middle turbinate, in order to attach the middle turbinates to the septum. The handle 112, activates the fastening module. In one embodiment the placement of the staple is performed under direct or remote endoscopic visualization.

Figure 2:
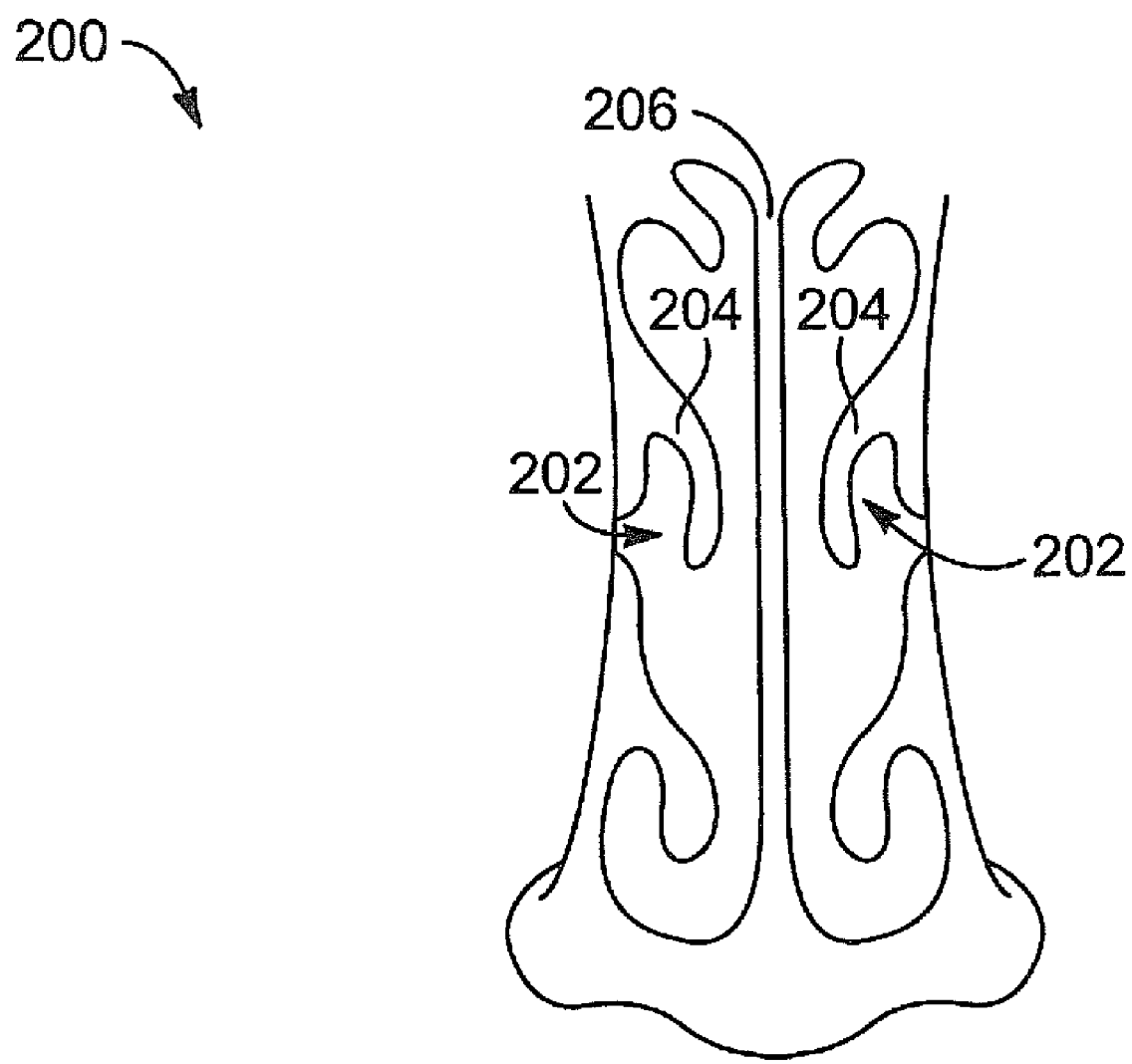
FIG. 2 is a perspective view with a cut away illustrating the anatomy of a nasal cavity.

Referring now to FIG. 2, FIG. 2 illustrates the general anatomy of a nasal cavity 200. When sinus surgery classically known as FESS for Functional Endoscopic Sinus Surgery is conducted, the sinus cavity is accessed through sinus opening 202 under the middle turbinate 204. When the surgery is completed, the middle turbinate 204 often bonds to the exterior wall of the nasal cavity 200, blocking the sinus opening 202 and preventing proper aeration and draining of the sinus.

To prevent this, a number of known processes are conducted, including abrading the medial surface of the middle turbinate 204 and the septum 206 of the nose and inserting packing material between the outer wall of the nasal cavity and the middle turbinate 204 so that the middle turbinate 204 will bond to the septum 206. This method has disadvantages, however, including patient discomfort and the tendency of packing to foster the growth of granulation tissue. To improve upon this, surgeons have stitched the two middle turbinates 204 together to the septum 206. However, this is a time consuming task, and the stitches are required to be removed afterward.

Figure 3:
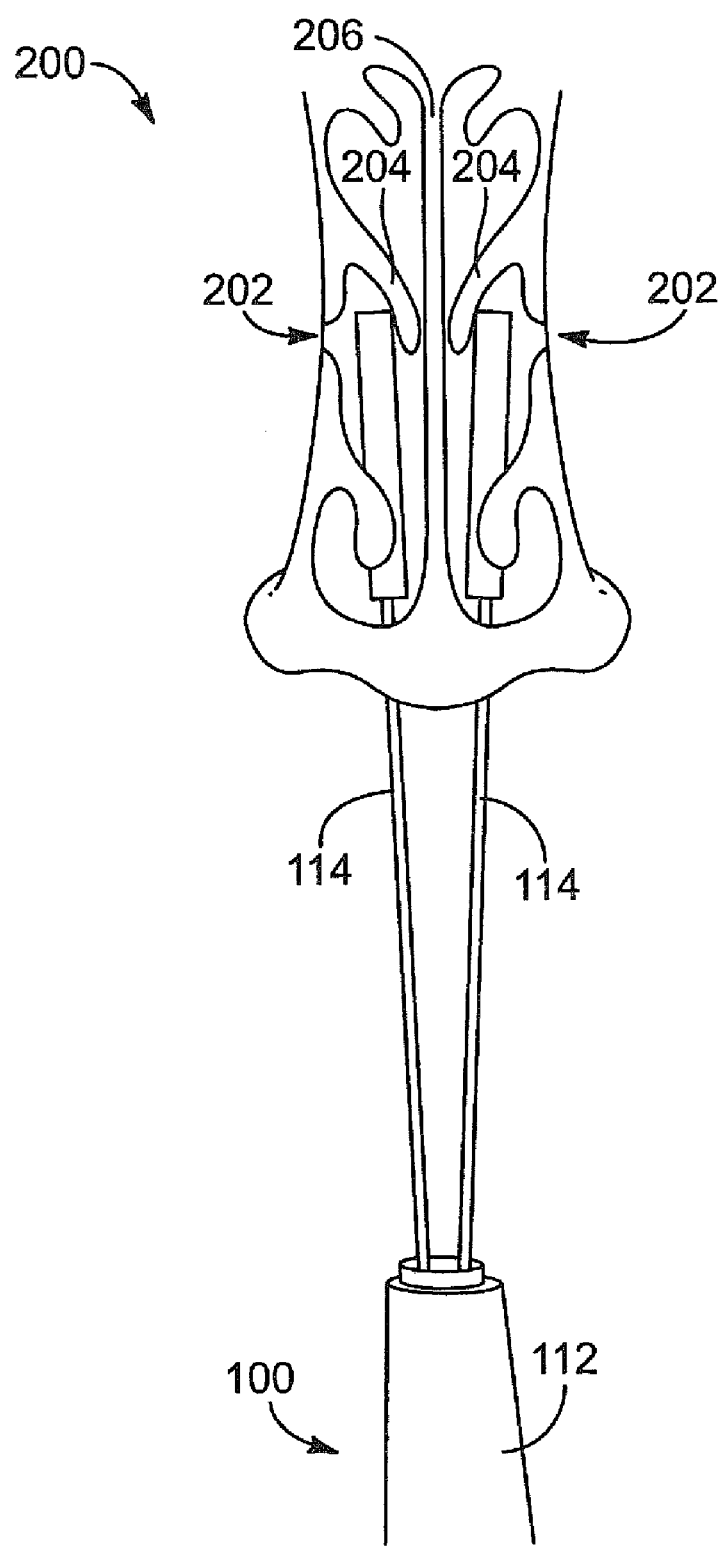
FIG. 3 is a perspective view with a cut away illustrating one embodiment of a middle turbinate medializer fastening the middle turbinates of two nasal cavities to a septum.
Figure 4:
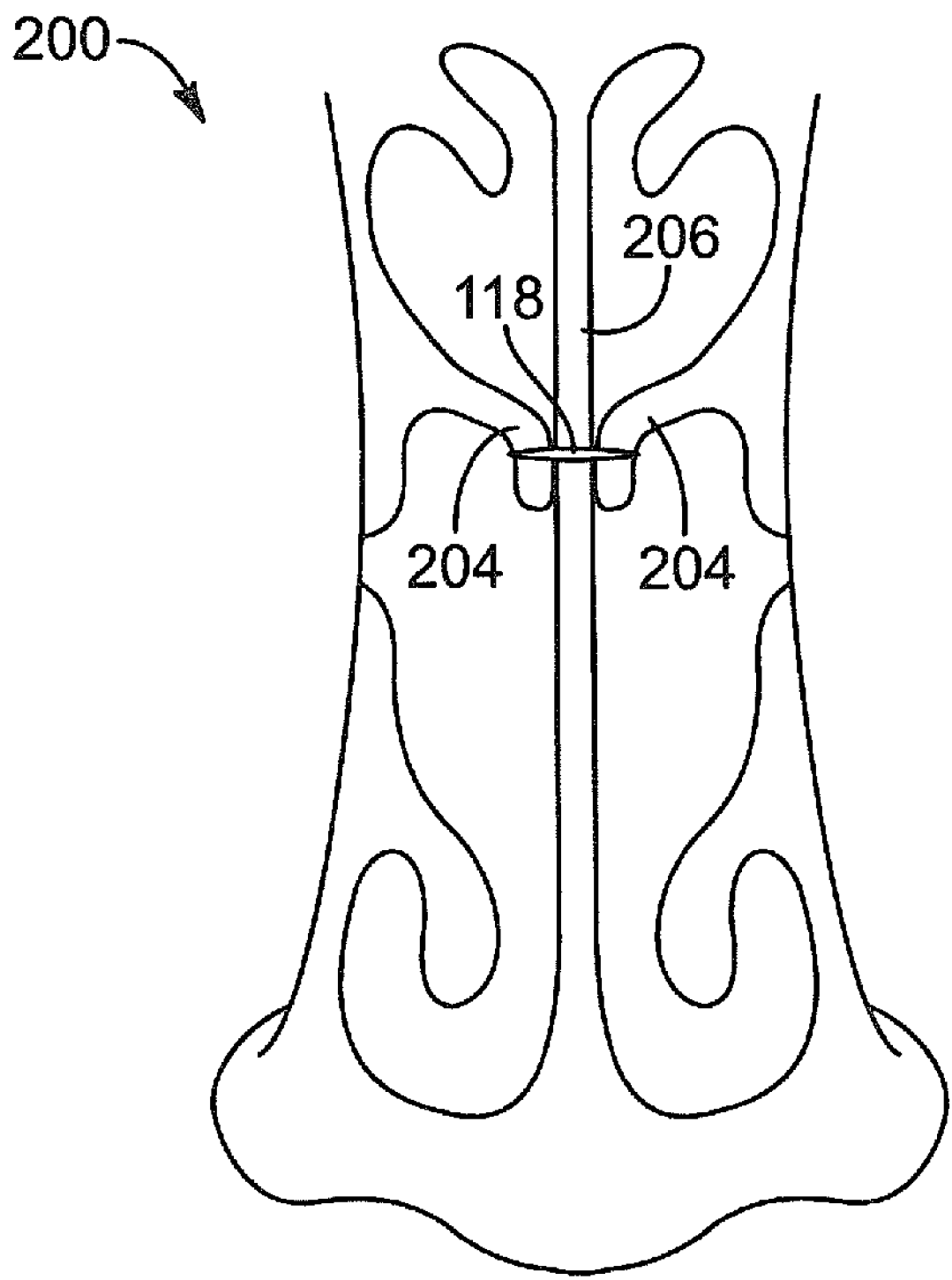
FIG. 4 is a perspective view with a cut away illustrating two middle turbinates fastened to a septum.

The present invention 100 enters into the nose with one prong 14 inserted in each nasal cavity 200 as illustrated in FIG. 3, and is used to staple, suture, or otherwise fasten the two middle turbinates 204 to each other and to the middle septum 206. In some cases both middle turbinates 204 are fastened to the septum 206, though in other cases only a single middle turbinate 204 may be fastened to the septum 206. Accordingly, when in operation, the trigger 122 (FIG. 1) is pulled, and the staple 118 is fastened to the base 120 through the septum 206 and middle turbinates 204, as illustrated in FIG. 4. In one embodiment, the staple 118 or suture is dissolvable and may be formed of an absorbable copolymer staple, as is well known in the art.

The operation prevents lateralization of the middle turbinate 204, with resulting adhesion and obstruction of the sinus opening 202 which is called synechiae. Furthermore, the invention may be used in various applications to correct nasal conditions. One such application may include fastening together various parts of the septum after septoplasty. Septoplasty is an operation that alters or removes portions of the supporting structures in the septum in order to correct defects or deformities in the nose. One example of a defect is a deviated septum.

Figure 5:
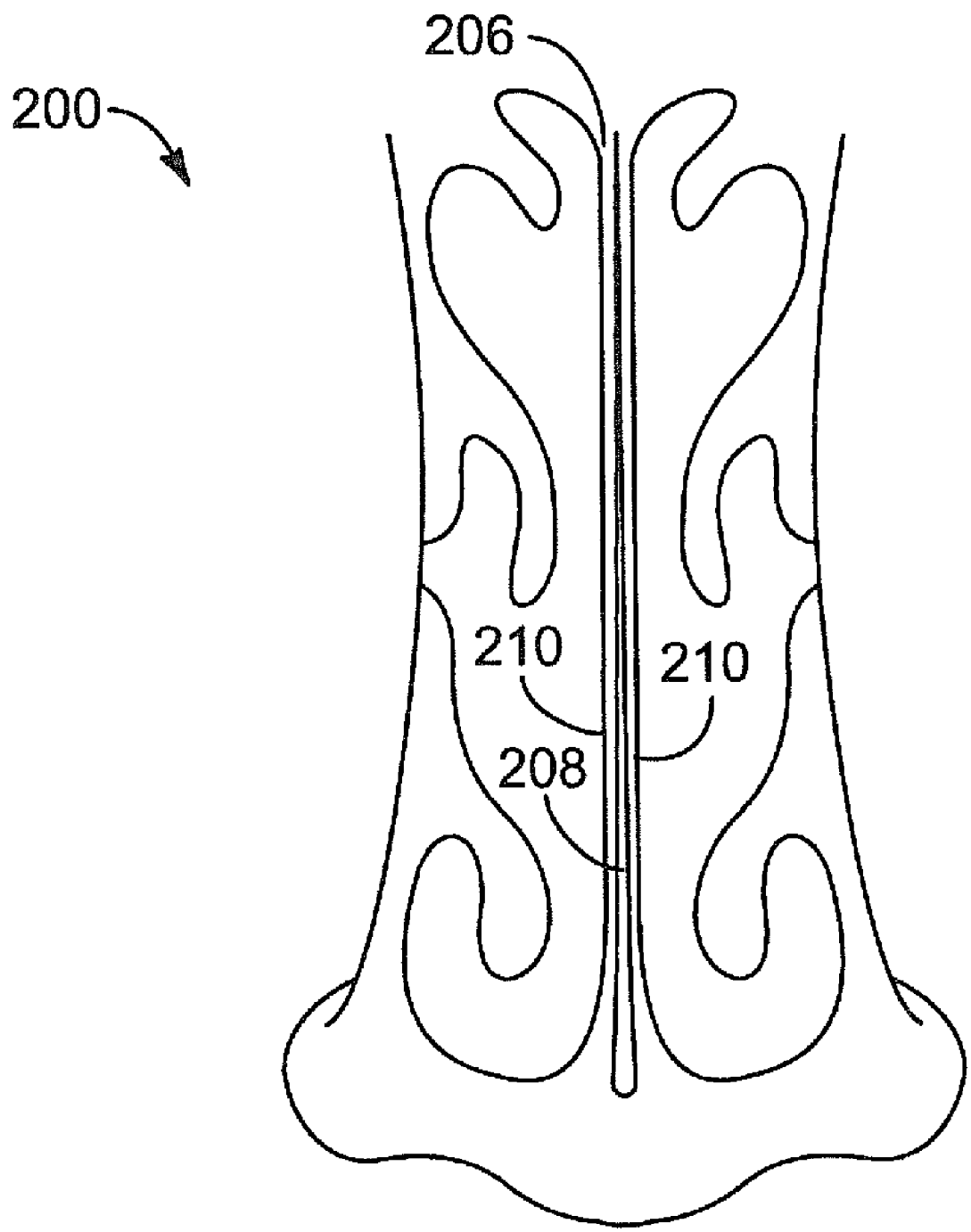
FIG. 5 is a perspective view with a cut away illustrating a nasal cavity with a normal septum.

FIG. 5 illustrates a nasal cavity 200 with a normal septum 206. The ideal nasal septum 206 is exactly midline and divides the left and right sides of the nose into passages of equal size. The supporting structure 208 is usually composed of cartilage or bony tissue and is covered by a membrane 210.

Figure 6:
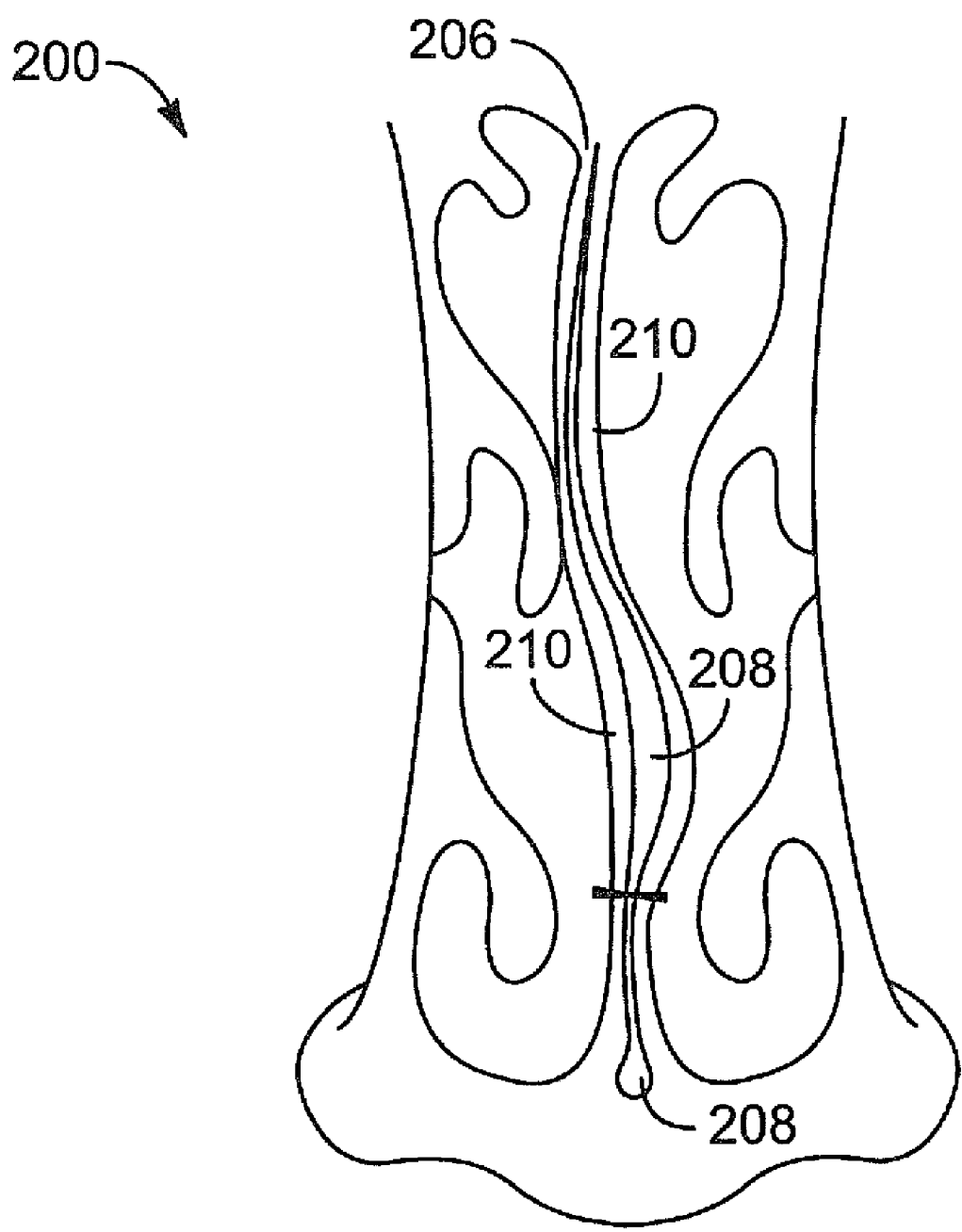
FIG. 6 is a perspective view with a cut away illustrating a nasal cavity with a deviated septum.

A deviated septum 206 occurs when the septum 206 is severely shifted away from the midline as illustrated in FIG. 6. In severe cases, a deviated septum 206 may block the nasal passage, consequently hindering breathing through the nose and contributing to frequent sinus infections. To treat this defect, septoplasty is usually performed, thereby removing the problematic areas of the supporting structure 208.

Figure 7:
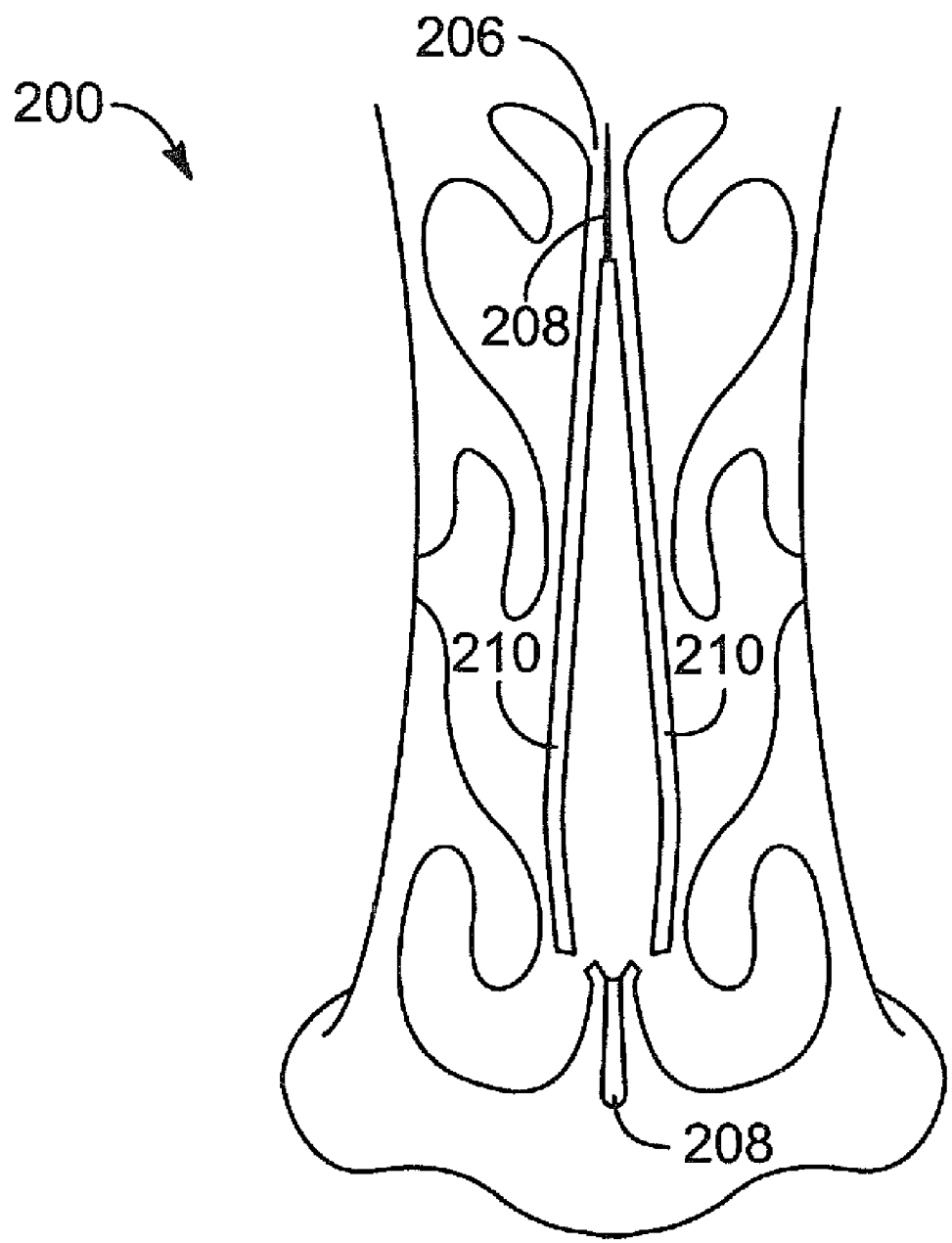
FIG. 7 is a perspective view with a cut away illustrating a septum with the cartilage or bony portion removed after septoplasty.

FIG. 7 illustrates a nasal cavity 200 with a portion of the cartilage/bony structure 208 removed from the septum 206. During the procedure, the membranes 210 are cut away from the hard tissue 208, forming mucoperichondrial flaps 210, which traditionally are sutured together; again, a difficult, time consuming task. However, the middle turbinate medializer 100 of the present invention may be used to reapproximate both mucoperichondrial flaps 210 after septoplasty.

Figure 8:
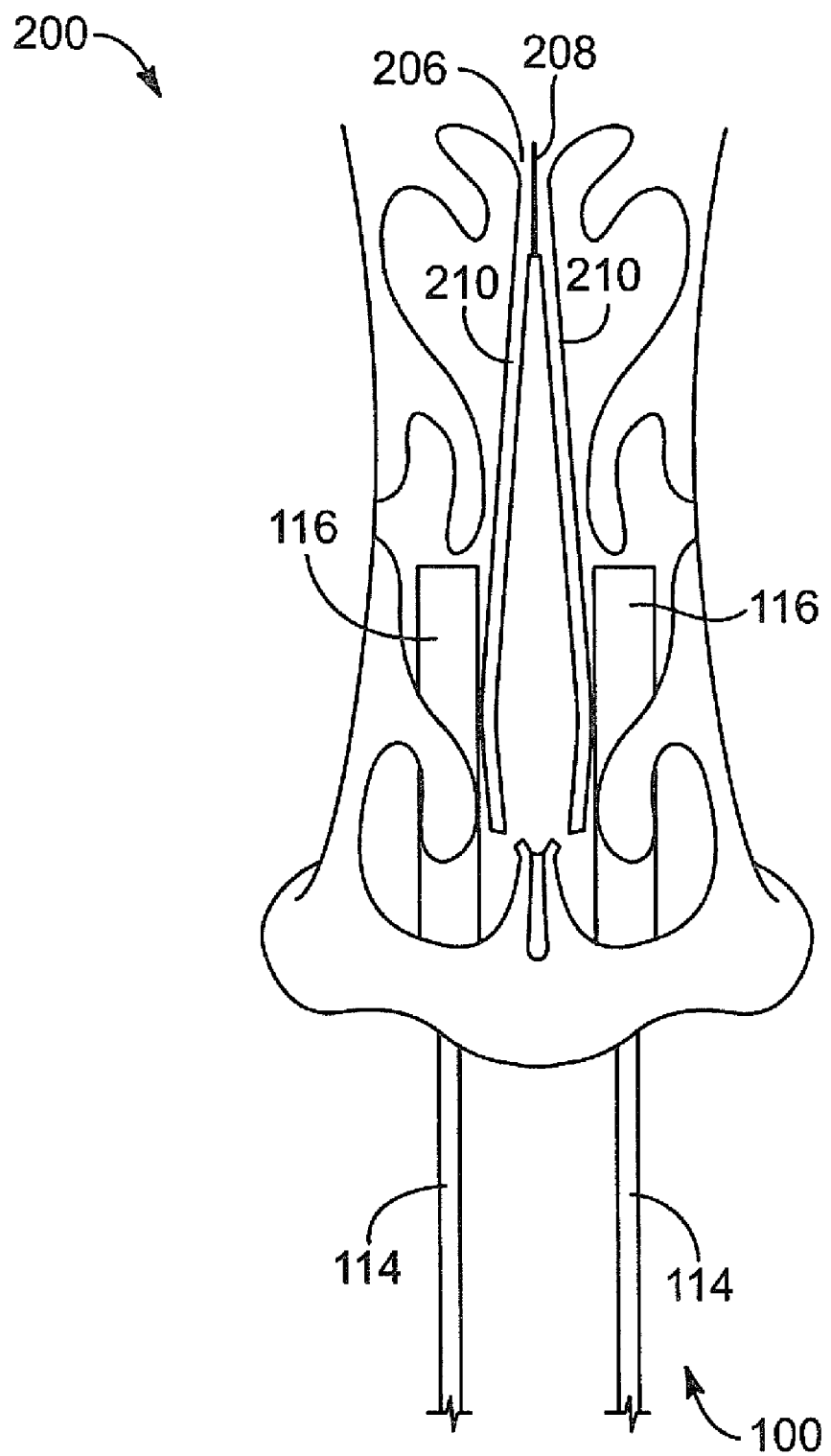
FIG. 8 is a perspective view with a cut away illustrating one embodiment of a middle turbinate medializer fastening a mucoperichondrial flap of the septum to another mucoperichondrial flap.
Figure 9:
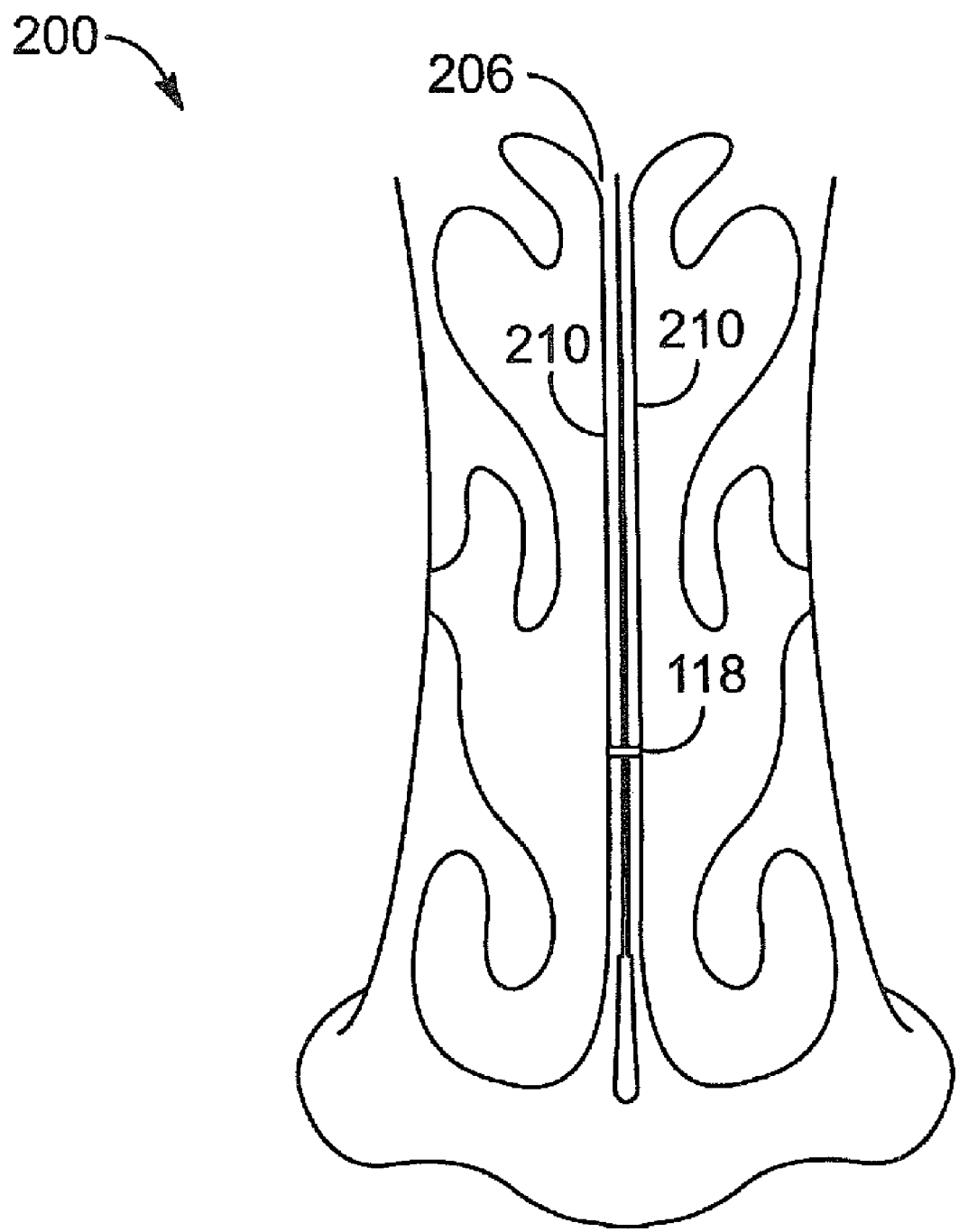
FIG. 9 is a perspective view with a cut away illustrating a nasal cavity with the mucoperichondrial flaps fastened together with a staple.

FIG. 8 illustrates a middle turbinate medializer 100 inserted through the nostrils to fasten the mucoperichondrial flaps 210 in place to allow the septum 206 to heal and return to a midline position. FIG. 9 depicts a staple 118 securing the flaps 210 of the septum 206. Of course, any number of staples 118 or sutures may be introduced to the nasal cavity using the present invention.

Figure 10:
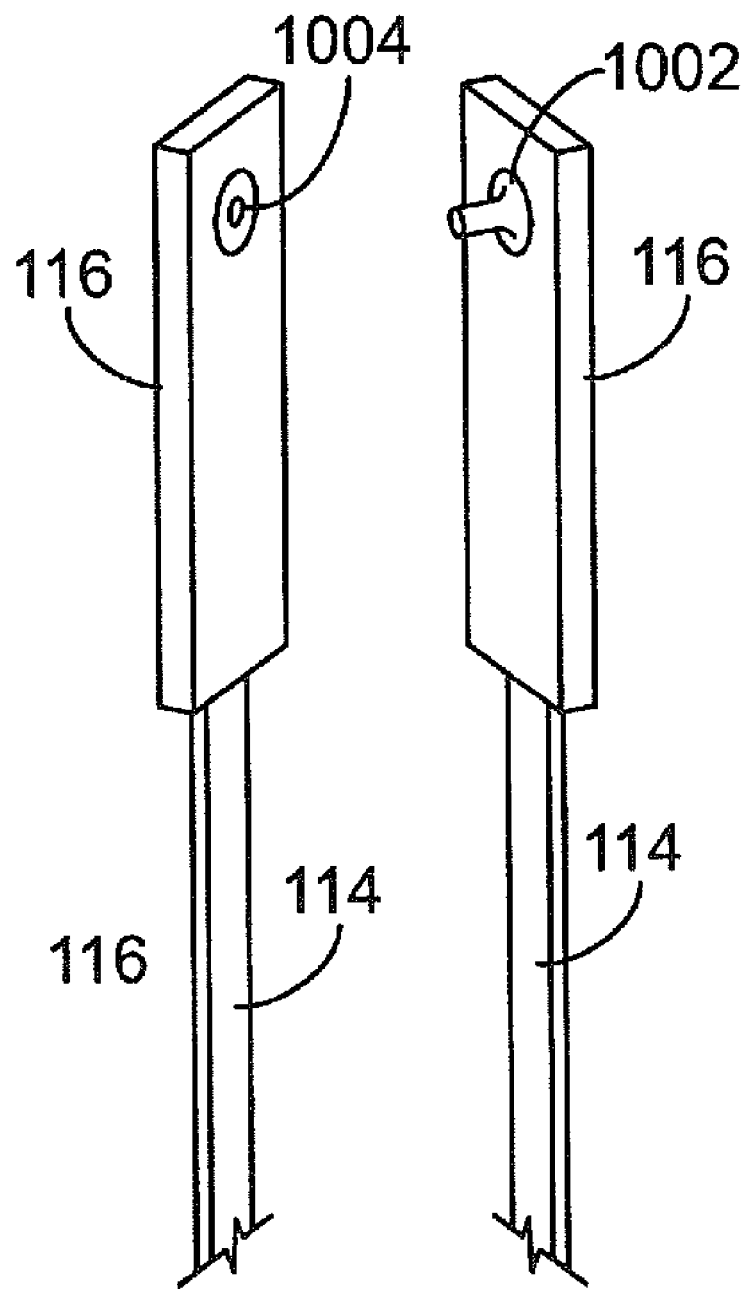
FIG. 10 is a perspective view of an embodiment of the prongs of a turbinate medializer configured to insert a rivet.

In a further embodiment, the medializer 100 may operate as a rivet gun which is pressed into one or both nasal cavities 200, and in effect, the turbinate 204 is riveted in place. FIG. 10 is a schematic drawing depicting the fastening ends 116 of prongs 114 filled with a rivet 1002 and a rivet receiver 1004. In a further embodiment the rivet may be comprised of bioabsorbable material.

Figure 11:
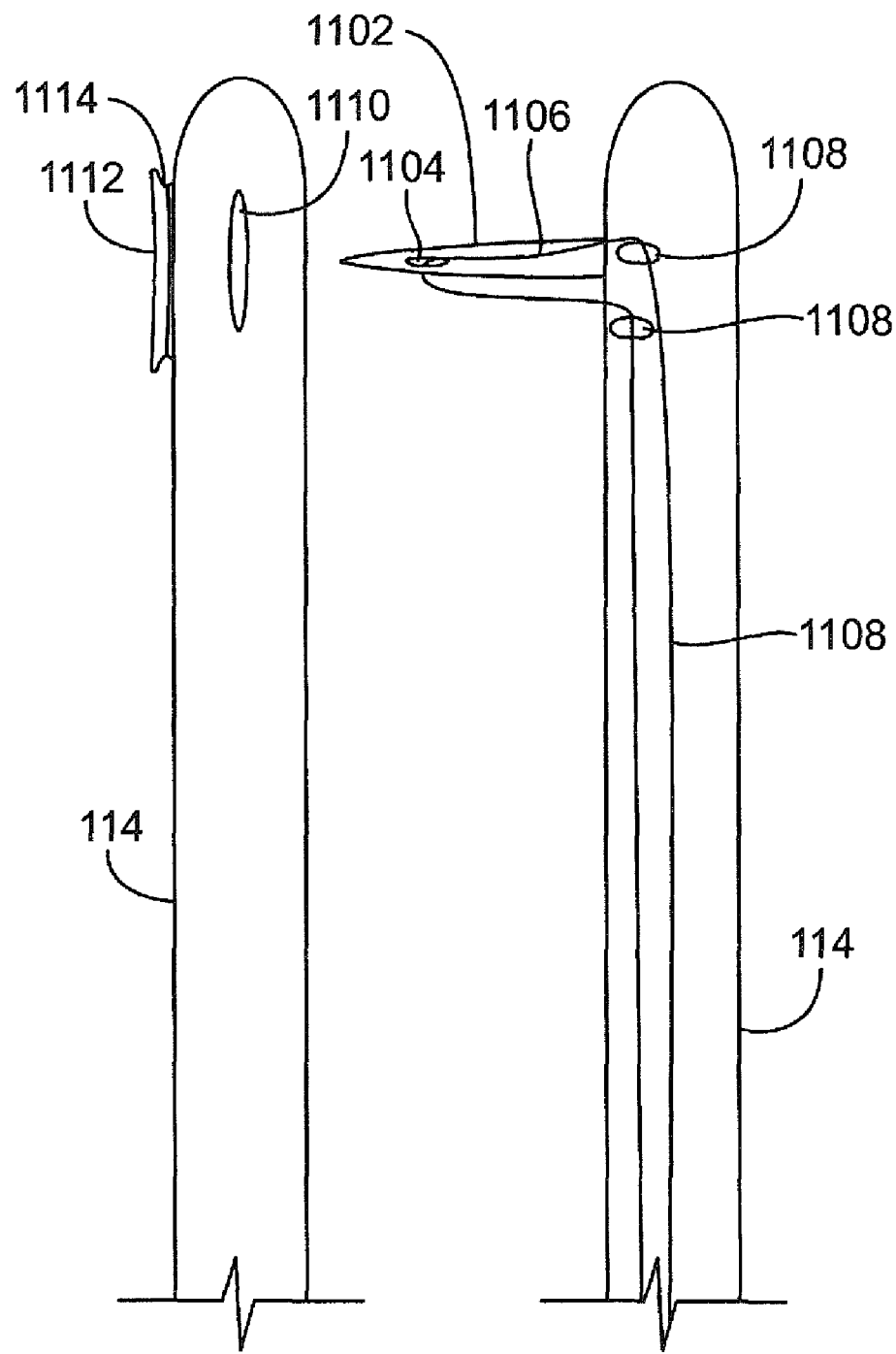
FIG. 11 is a perspective view of an embodiment of the prongs of a turbinate medializer configured to apply a suture.

Sutures may be fastened in a like manner. FIG. 11 is a schematic drawing depicting a needle, 1102, mounted perpendicularly to a prong 114. A thread 1106 passes through a thread guide 1108, through a needle eye 1104 and back through thread guide 1108. A hole 1110 on the opposite prong 114 communicates with a bobbin assembly 1112 carrying bobbin thread 1114. In the depicted embodiment the prongs are inserted into the nasal cavity and the needle 1102 is activated, piercing the turbinates and septum, passing through the hole 1110 and engaging the bobbin 1112, causing the thread 1106 to loop and knot with the bobbin thread 1114, forming a suture. In a further embodiment the suture is placed under direct endoscopic visualization. In a further embodiment the suture may be performed with bioabsorbable thread.

Figure 12:
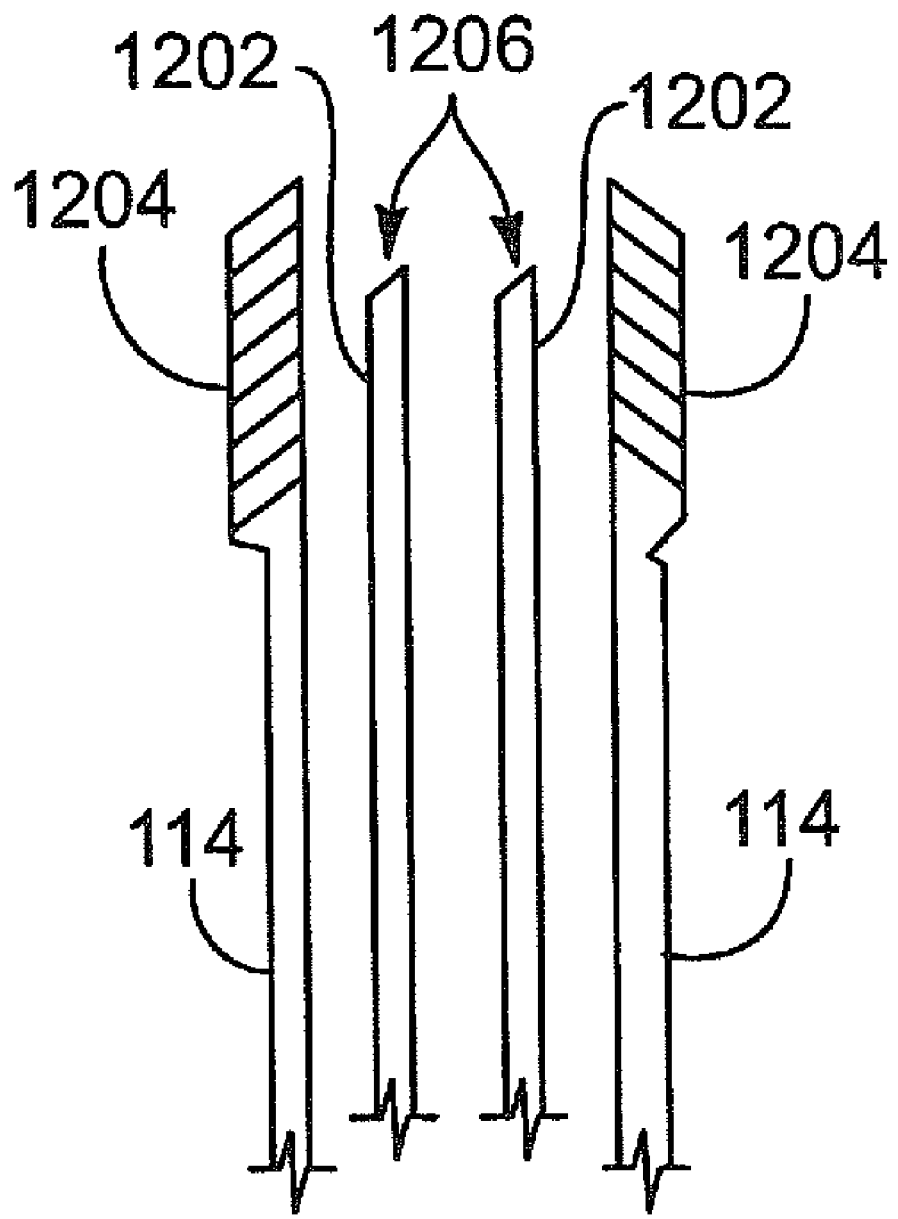
FIG. 12 is a perspective view of an embodiment of the prongs of a turbinate medializer configured to apply adhesive.
Figure 13:
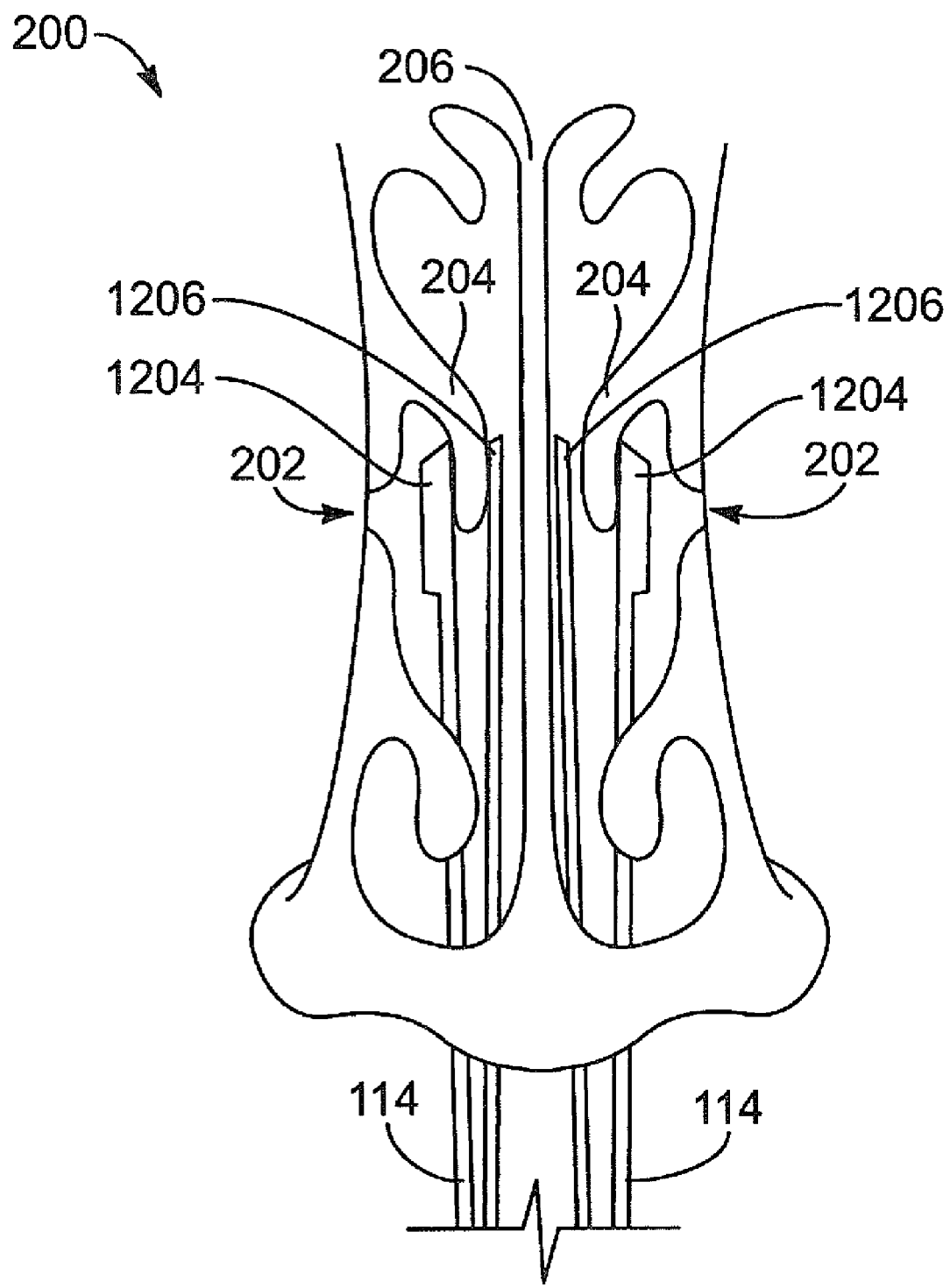
FIG. 13 is a perspective view of an embodiment of the prongs of an adhesive configured turbinate medializer inserted in a nasal cavity.

Various types of tissue adhesive may also be applied to secure the turbinate to the septum. FIG. 12 depicts an embodiment in which hollow rods 1202 deposit adhesive 1206 between the turbinate and the septum. Pressure pads 1204 mounted on prongs 114 then close against the turbinates, holding them against the septum while the adhesive sets. FIG. 13 depicts the device in place in a nasal cavity 200. Adhesive 1206 flows through hollow rods 1202 to be deposited between the middle turbinates 204 and the septum 206. In one embodiment rods deposit the adhesive and then withdraw. Pressure pads 1204 hold the turbinates 204 against the septum 206 during the setting of the adhesive.

Figure 14:
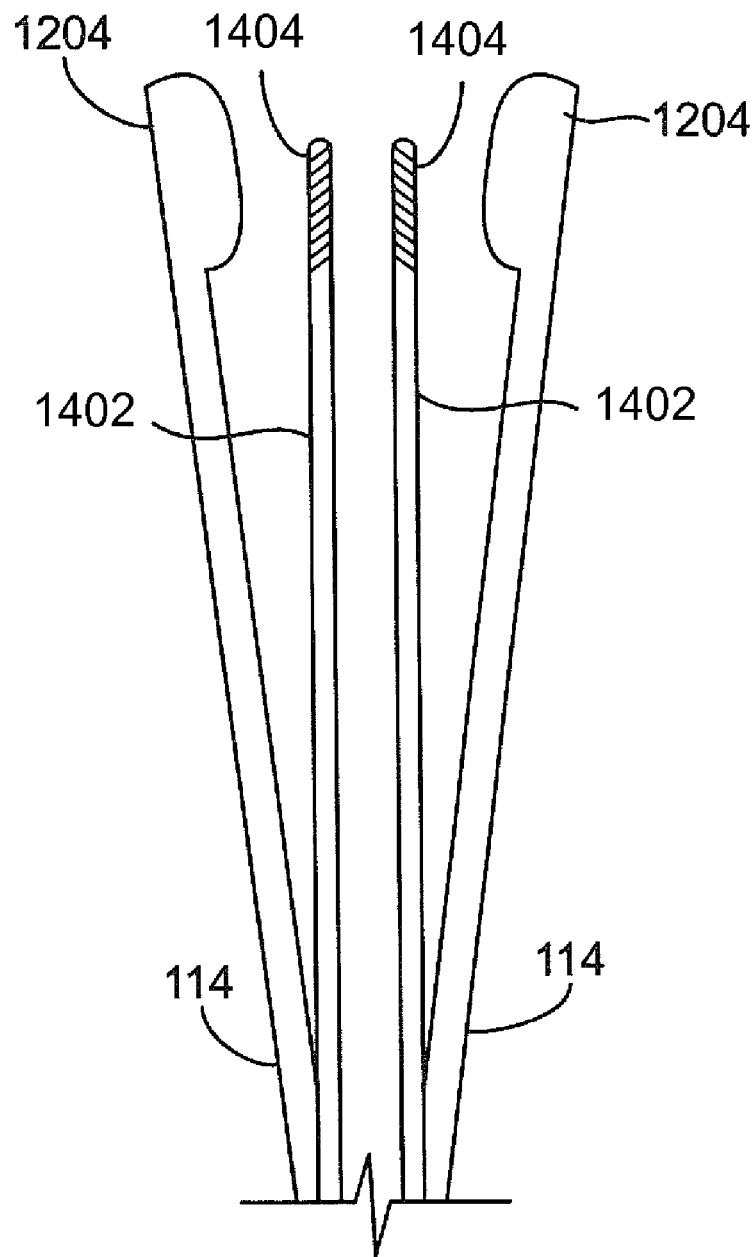
FIG. 14 is a perspective view of an embodiment of the prongs of an embodiment of a cauterizing turbinate medializer.
Figure 15:
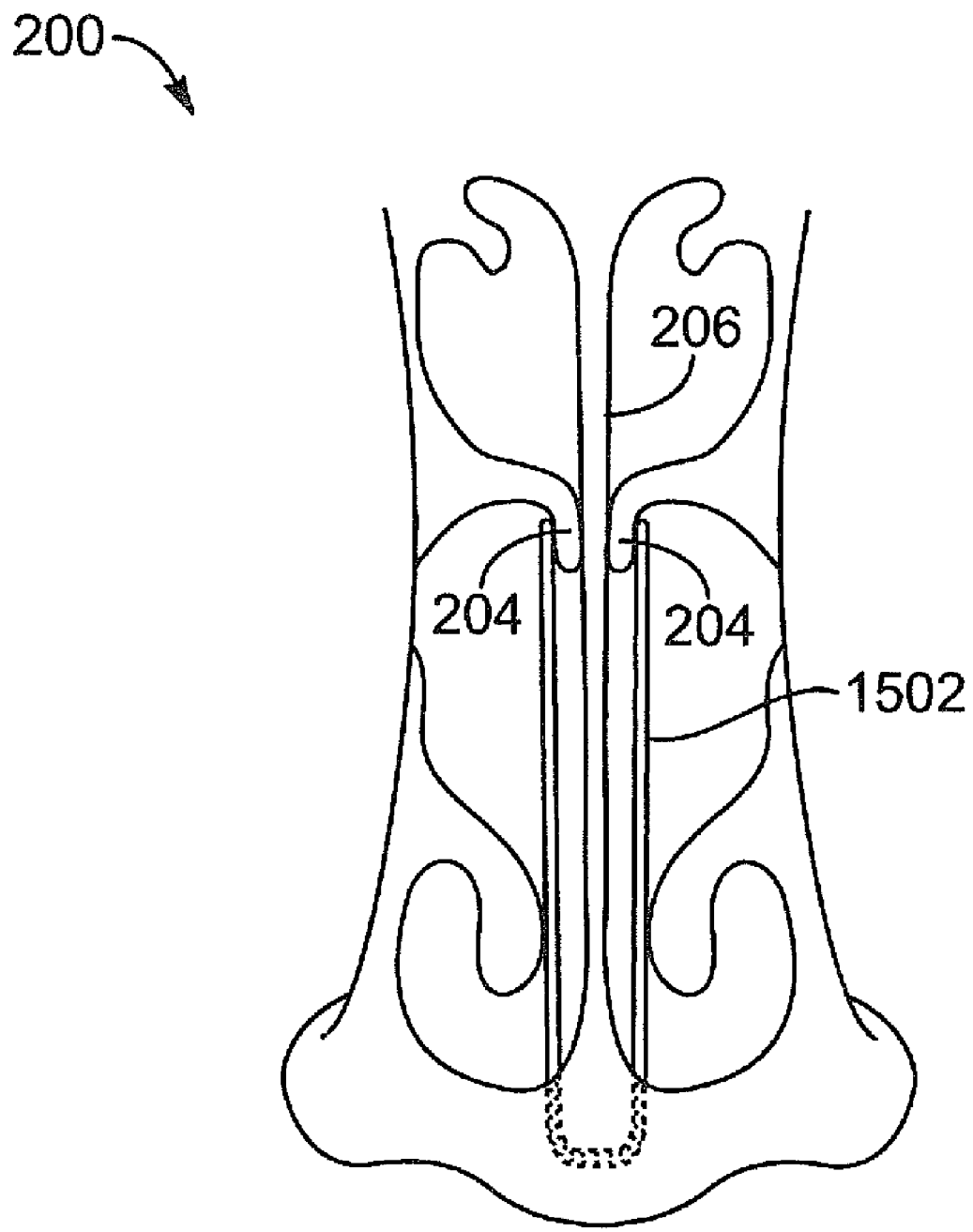
FIG. 15 is a perspective view of a nasal clamp securing the middle turbinates during adhesion of the cauterization.

Cauterization may also create an adhesion between the middle turbinates and the septum. FIG. 14 depicts an embodiment of a cauterization iron. Heat wands 1402 carry heat tips 1404. Pressure pads 1204 hold the turbinate and septul tissues against the heat tips during cauterization. In a further embodiment a temporary clamp 1502 holds the middle turbinates against the septum while the burns adhere as illustrated in FIG. 15.

Figure 16:
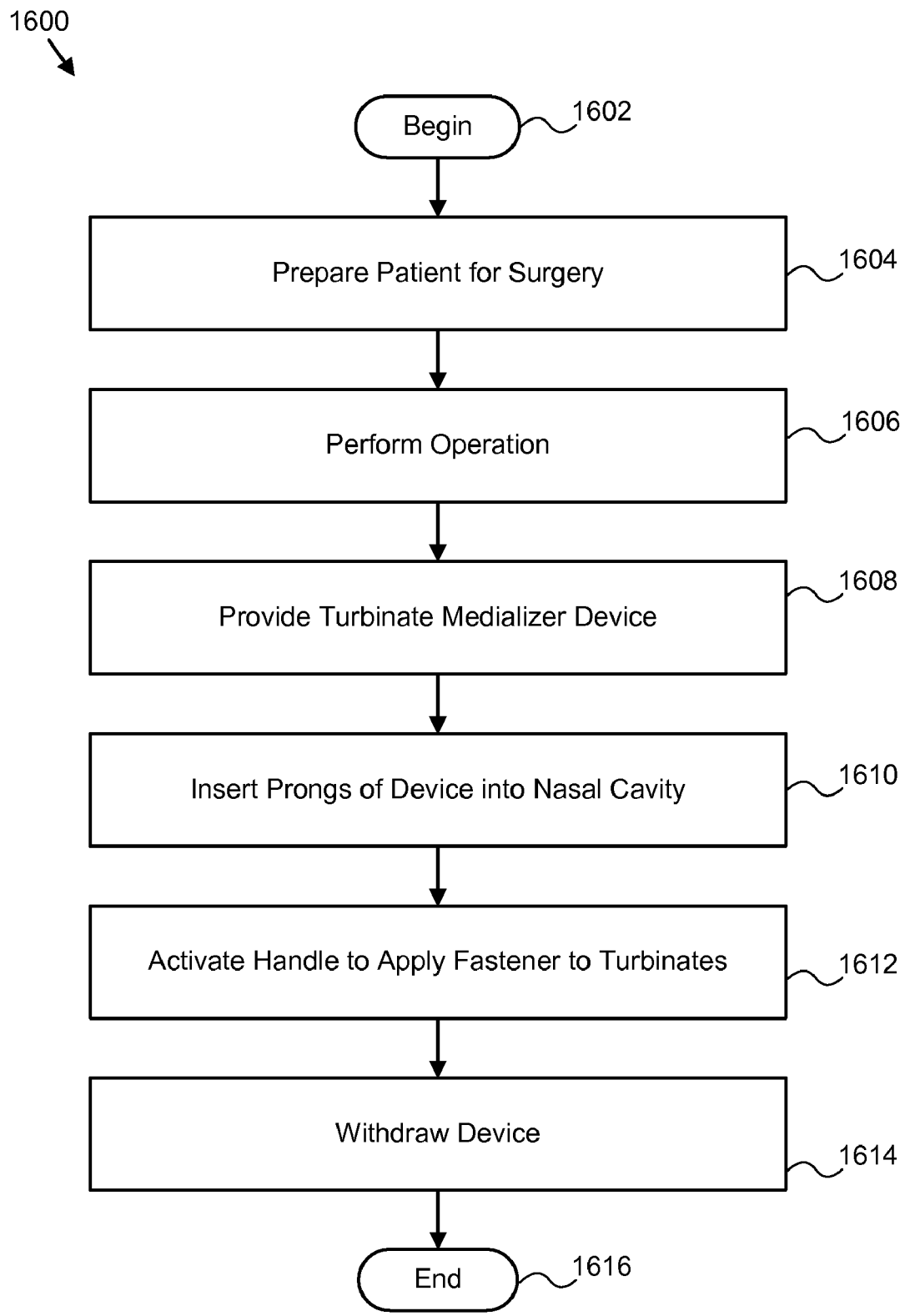
FIG. 16 is a schematic flow chart diagram illustrating a method in accordance with the present invention.

FIG. 16 is a schematic block diagram depicting a method 1600 in accordance with the present invention. The method 1600 begins 1602 and comprises the steps of: preparing a patient for surgery 1604; performing an operation 1606; providing the turbinate medializer device 1608; inserting the prongs of the device into the nasal cavity 1610; activating the handle of the device to apply the fastener to the turbinates 1612; and withdrawing the device 1614. The method 1600 then ends 1616.

All of the above procedures may be applied to a single turbinate or a pair of turbinates with equal effectiveness. The present invention may be embodied in other specific forms without departing from its spirit or essential characteristics. The described embodiments are to be considered in all respects only as illustrative and not restrictive.

What is claimed is:

1. A method for medializing a middle turbinate to a septum, the method comprising:
    providing a medical device configured to attach the turbinate to the septum, the medical device comprising a handle and at least one prong, the handle configured to control the deployment of a fastener, the at least one prong configured to enter a nasal cavity between the turbinate and an outer wall of the nasal cavity;
    inserting the at least one prong of the medical device into the nasal cavity;
    activating the handle of the medical device to apply the fastener to the turbinate, the fastener attaching the turbinate to the septum; and
    withdrawing the medical device.

2. The method of claim 1, further comprising piercing the turbinate and the septum with a needle, wherein a thread is disposed through a hole in the needle, the thread comprising the fastener configured to attach the turbinate to the septum.

3. The method of claim 2, wherein the thread is bioabsorbable.

4. The method of claim 1, further comprising endoscopically viewing the placement of the fastener.

5. The method of claim 1, further comprising providing a needle mounted perpendicular to the at least one prong, the needle configured to receive a thread, the thread comprising the fastener configured to attach the turbinate to the septum when the handle is activated.

6. The method of claim 5, further comprising providing a bobbin assembly disposed on a second prong, the second prong disposed opposite the at least one prong, the bobbin assembly carrying a bobbin thread, the needle configured to engage the bobbin causing the thread to loop and knot with the bobbin thread forming a suture when the handle is activated.

7. The method of claim 1, further comprising attaching a first middle turbinate and a second middle turbinate to the septum.

8. The method of claim 1, further comprising activating the handle of the medical device to apply the fastener to a mucoperichondrial flap to reapproximate the mucoperichondrial flap.

9. A method for medializing a first middle turbinate and a second middle turbinate to a septum, the method comprising:
provproviding a medical device configured to attach the first middle turbinate and the second middle turbinate to the septum, the medical device comprising a handle and at least one prong, the handle configured to control the deployment of a fastener, the at least one prong configured to enter a nasal cavity between at least one middle turbinate and an outer wall of the nasal cavity;
inserting the at least one prong of the medical device into the nasal cavity;
activating the handle of the medical device to apply a fastener to the turbinate, the fastener attaching the turbinate to the septum; and
withdrawing the medical device.

10. The method of claim 9, further comprising piercing the first turbinate, the second turbinate and the septum with a needle, wherein a thread is disposed through a hole in the needle, the thread comprising the fastener configured to attach the first turbinate and the second turbinate to the septum.

11. The method of claim 10, wherein the thread is bioabsorbable.

12. The method of claim 9, further comprising endoscopically viewing the placement of the fastener.

13. The method of claim 9, further comprising providing a needle mounted perpendicular to the at least one prong, the needle configured to receive a thread, the thread comprising the fastener configured to attach the first turbinate and the second turbinate to the septum when the handle is activated.

14. The method of claim 13, further comprising providing a bobbin assembly disposed on a second prong, the second prong disposed opposite the at least one prong, the bobbin assembly carrying a bobbin thread, the needle configured to engage the bobbin causing the thread to loop and knot with the bobbin thread forming a suture when the handle is activated.

15. The method of claim 9, further comprising activating the handle of the medical device to apply the fastener to a mucoperichondrial flap to reapproximate the mucoperichondrial flap.

16. A method for medializing a middle turbinate to a septum, the method comprising:
providing a medical device configured to attach the middle turbinate to the septum, the medical device comprising a handle attached to a first prong and a second prong, the handle configured to control the deployment of a thread, the first prong and the second prong configured to enter a nasal cavity between the middle turbinate and an outer wall of the nasal cavity;
providing a needle mounted perpendicular to the first prong, the needle configured to receive the thread;
providing a bobbin assembly disposed on the second prong, the second prong disposed opposite the first prong, the bobbin assembly carrying a bobbin thread;
inserting the at least one prong of the medical device into the nasal cavity;
activating the handle of the medical device to cause the needle to engage the bobbin thread to attach the middle turbinate to the septum; and
withdrawing the medical device.

17. The method of claim 16, wherein the medical device is further configured to attach a second middle turbinate to the septum, the method further comprising piercing the middle turbinate, the second middle turbinate and the septum with the needle, the needle configured to engage the bobbin causing the thread to loop and knot with the bobbin thread forming a suture when the handle is activated.

18. The method of claim 17, wherein the thread is bioabsorbable.

19. The method of claim 16, further comprising endoscopically viewing the placement of the thread.

20. The method of claim 16, wherein the first prong and the second prong are configured to receive the first turbinate, the second turbinate and the septum between the first prong and the second prong.

* * * * *